(12) United States Patent
Yoo et al.

(10) Patent No.: US 10,605,983 B2
(45) Date of Patent: Mar. 31, 2020

(54) NOISE REDUCTION COLLIMATOR AND IMAGING CATHETER SYSTEM

(71) Applicants: Industry-University Cooperation Foundation Hanyang University, Seoul (KR); Korea University Research and Business Foundation, Seoul (KR); KOREA ADVANCED INSTITUTE OF SCIENCE AND TECHNOLOGY, Daejeon (KR)

(72) Inventors: Hong Ki Yoo, Seoul (KR); Jin Won Kim, Seoul (KR); Wang Yuhl Oh, Daejeon (KR); Min Woo Lee, Suwon-si (KR); Tae Shik Kim, Daejeon (KR)

(73) Assignees: Industry-University Cooperation Foundation Hanyang University, Seoul (KR); Korea University Research and Business Foundation, Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/080,330

(22) PCT Filed: Feb. 28, 2017

(86) PCT No.: PCT/KR2017/002181
§ 371 (c)(1),
(2) Date: Aug. 28, 2018

(87) PCT Pub. No.: WO2017/150879
PCT Pub. Date: Sep. 8, 2017

(65) Prior Publication Data
US 2019/0072713 A1 Mar. 7, 2019

(30) Foreign Application Priority Data
Feb. 29, 2016 (KR) .................. 10-2016-0024072

(51) Int. Cl.
*G02B 6/036* (2006.01)
*A61B 5/00* (2006.01)
(Continued)

(52) U.S. Cl.
CPC .......... *G02B 6/036* (2013.01); *A61B 5/0066* (2013.01); *A61B 5/0071* (2013.01);
(Continued)

(58) Field of Classification Search
None
See application file for complete search history.

(56) References Cited

U.S. PATENT DOCUMENTS 5,167,686 A * 12/1992 Wong .................. A61B 18/245
600/342
6,335,822 B1 * 1/2002 Toyohara ........... G02B 6/03605
359/337
(Continued)

FOREIGN PATENT DOCUMENTS

CN 101666890 A * 3/2010 ............... G02B 6/32
JP 2000-252559 A 9/2000
(Continued)

OTHER PUBLICATIONS

Notification of Reason for Refusal for Korean Patent Application No. 10-2016-0024072 dated Mar. 16, 2017.
(Continued)

*Primary Examiner* — Rhonda S Peace
(74) *Attorney, Agent, or Firm* — Sughrue Mion, PLLC

(57) ABSTRACT

Disclosed are a collimator for reducing noise of a scanned image and an imaging catheter system comprising the same. The disclosed noise attenuation collimator comprises: a transparent tube having a diameter larger than a cladding diameter of double-clad fiber, wherein a coatingless region of the double-clad fiber is inserted into the transparent tube; and a first resin layer which is applied to an exterior of the transparent tube and has a refractive index lower than the refractive index of the transparent tube.

4 Claims, 5 Drawing Sheets

(51) Int. Cl.
    *A61B 5/0215* (2006.01)
    *G02B 6/293* (2006.01)
    *G02B 6/02* (2006.01)
(52) U.S. Cl.
    CPC .......... *A61B 5/0086* (2013.01); *A61B 5/0215* (2013.01); *A61B 5/6852* (2013.01); *A61B 5/6876* (2013.01); *A61B 5/7203* (2013.01); *G02B 6/02* (2013.01); *G02B 6/293* (2013.01); *A61B 2505/05* (2013.01); *A61B 2562/0233* (2013.01); *A61B 2562/223* (2013.01)

(56) References Cited

U.S. PATENT DOCUMENTS

| | | | | |
|---|---|---|---|---|
| 7,306,376 | B2* | 12/2007 | Scerbak | G02B 6/4296 385/76 |
| 8,027,557 | B2* | 9/2011 | Frith | G02B 6/14 385/124 |
| 8,611,708 | B2* | 12/2013 | Engelberth | G02B 6/4296 385/28 |
| 2016/0285227 | A1* | 9/2016 | Farrow | H01S 3/0675 |
| 2018/0310826 | A1* | 11/2018 | Yoo | A61B 5/0084 |
| 2018/0348439 | A1* | 12/2018 | Yamada | G01B 9/02091 |
| 2019/0072713 | A1* | 3/2019 | Yoo | A61B 5/00 |

FOREIGN PATENT DOCUMENTS

| | | |
|---|---|---|
| JP | 3762557 B2 | 4/2006 |
| JP | 2008-171985 A | 7/2008 |
| KR | 10-1352960 B1 | 1/2014 |
| KR | 10-1397272 B1 | 5/2014 |

OTHER PUBLICATIONS

International Search Report for PCT/KR2017/002181 dated May 22, 2017 [PCT/ISA/210].

* cited by examiner

<Prior Art>

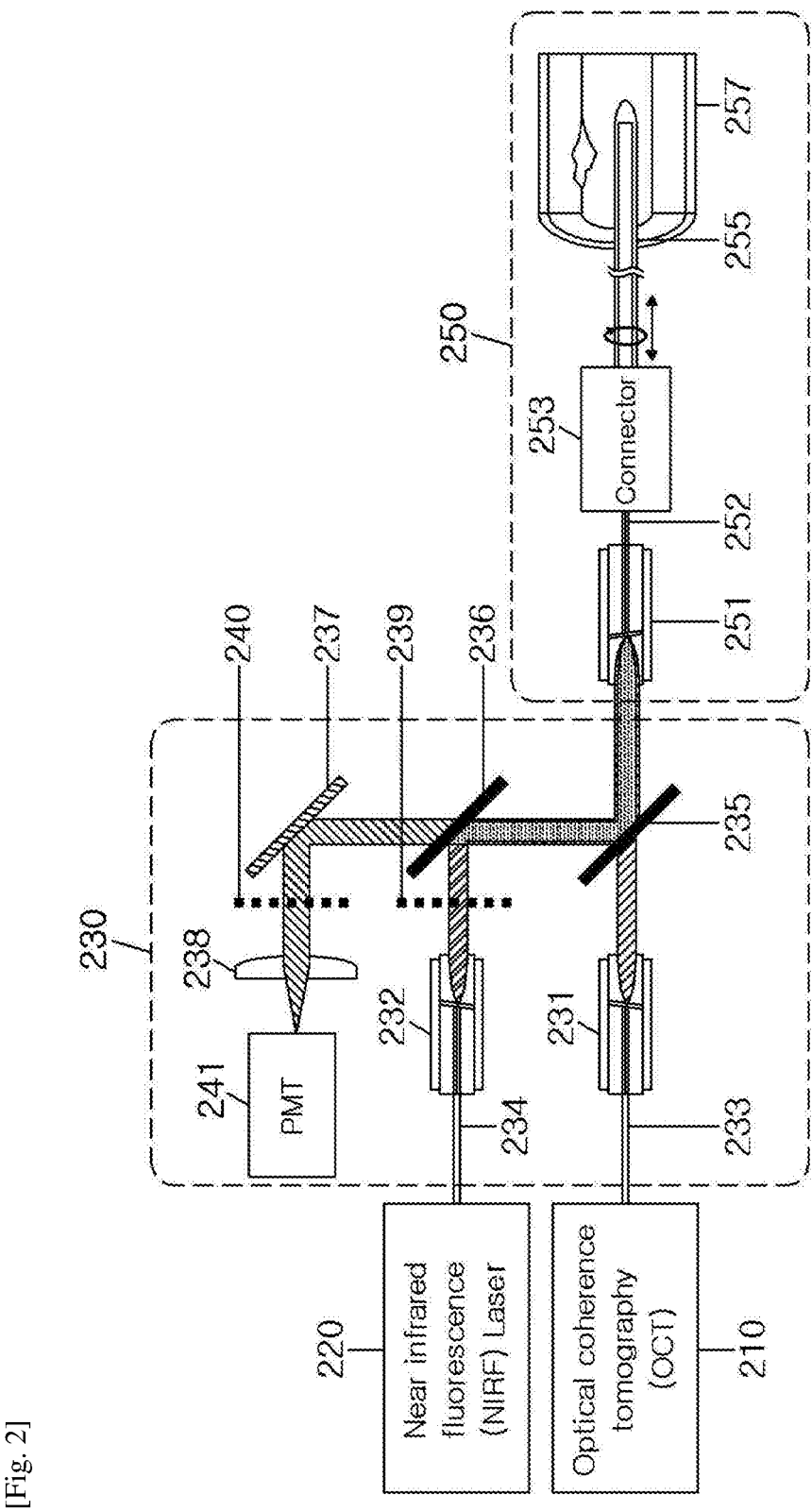
[Fig. 2]

[Fig. 3]
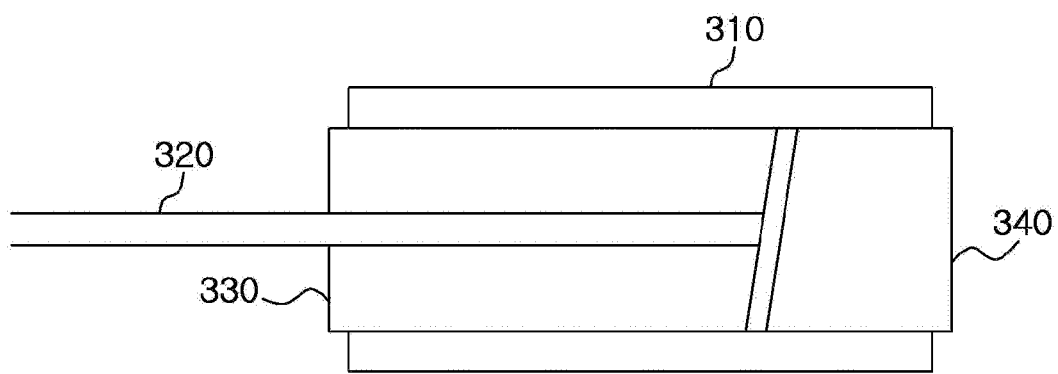
[Fig. 4]
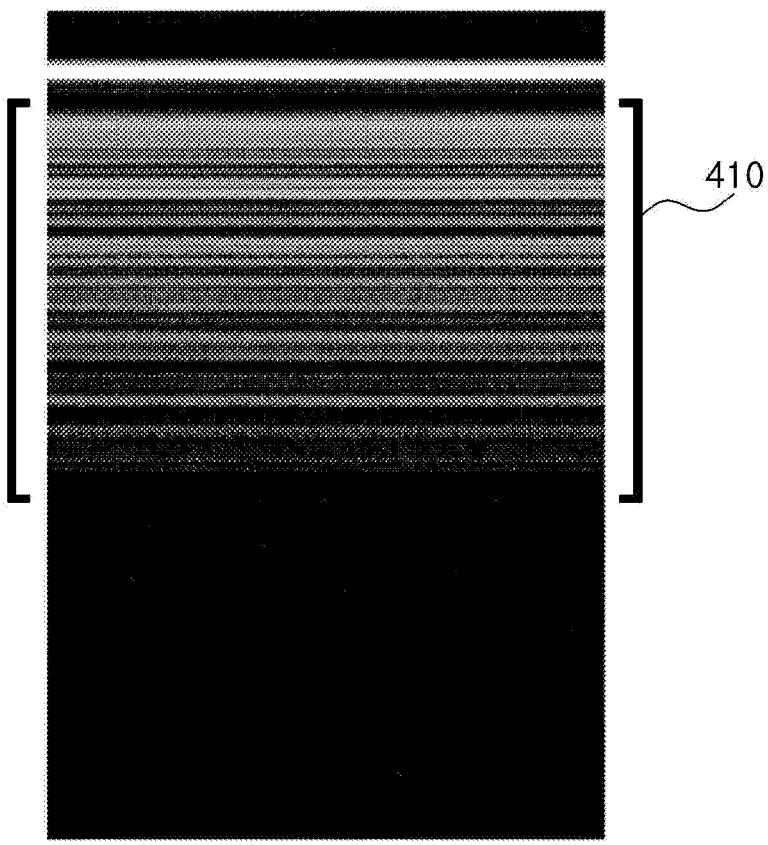

[Fig. 5]
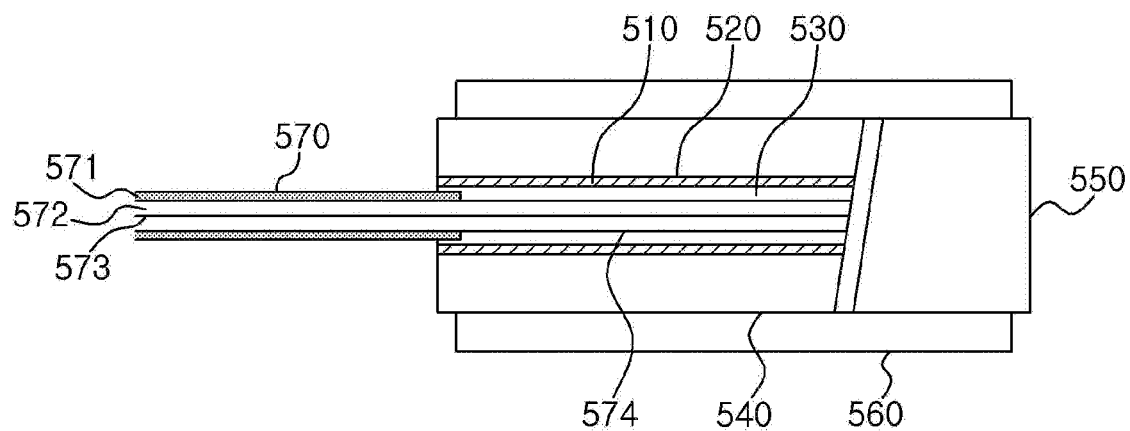
[Fig. 6]
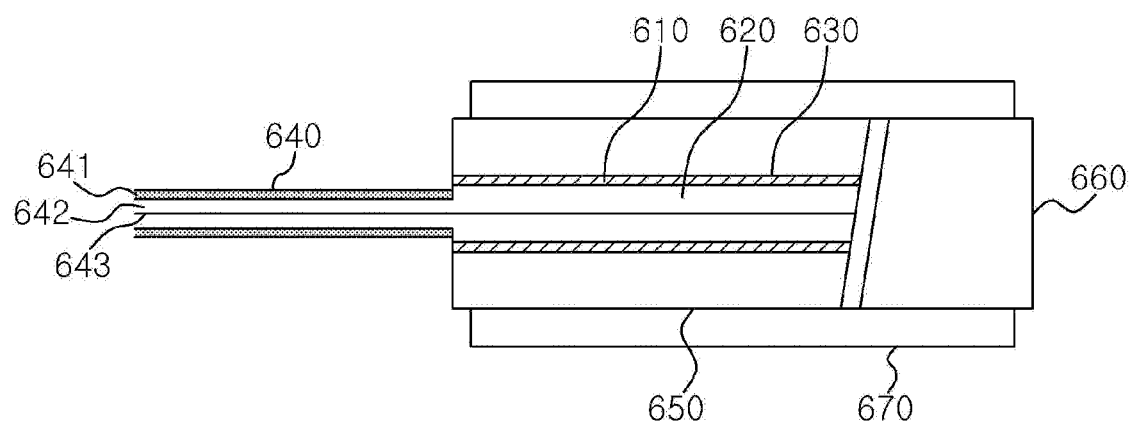

[Fig. 7]
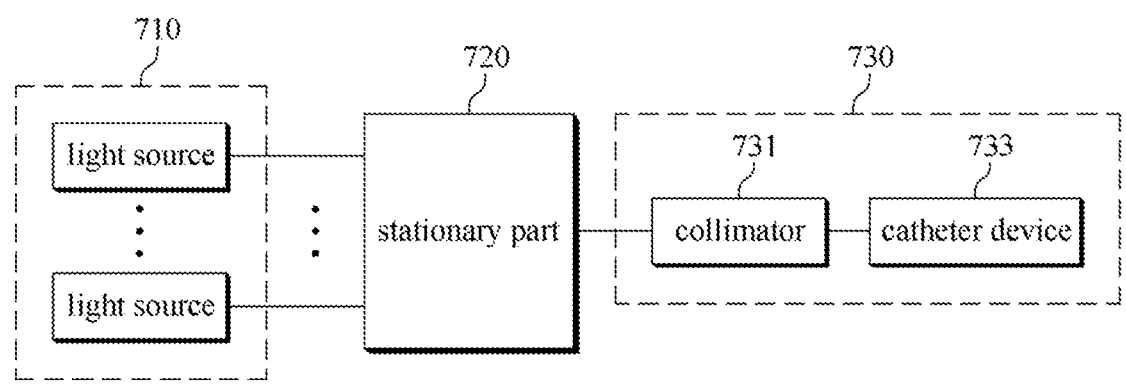
[Fig. 8]
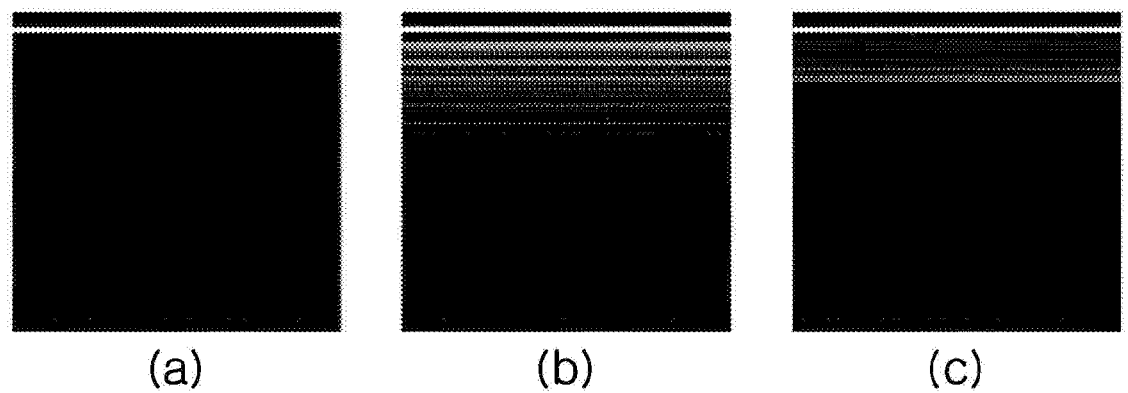
(a)　　　　　　　(b)　　　　　　　(c)

NOISE REDUCTION COLLIMATOR AND IMAGING CATHETER SYSTEM

BACKGROUND

1. Technical Field

The present invention relates to a collimator and an imaging catheter system including the same, more particularly to a collimator and an imaging catheter system including the collimator that can reduce noise in a scanned image.

2. Description of the Related Art

The related art associated with the imaging catheter, which is used for diagnosing cardiovascular diseases, etc., includes ultrasound techniques, near-infrared imaging techniques, optical coherence tomography techniques, etc., where many such techniques have been commercialized and are being utilized in clinics.

Ultrasound techniques, which involve inserting a device in the form of a catheter into a sample such as a blood vessel, etc., to obtain cross-sectional images of the blood vessel, are still the most widely utilized in hospitals for intravascular imaging. Since ultrasonic technology is used, the resolution is low, at a level of about 100 µm, the contrast is low also, and the imaging speed is slow, at about 30 seconds.

Near-infrared imaging techniques may involve identifying whether or not there are lipids in the inner walls of a blood vessel via a spectroscopic method using near-infrared light, and recently, a near-infrared imaging technique was combined with an intravascular ultrasound technique to be implemented in a single catheter.

Optical coherence tomography (OCT) techniques, similar to intravascular ultrasonic techniques, involve inserting a device in the form of a catheter into a blood vessel to emit light into the blood vessel and obtaining tomographic images of the blood vessel by analyzing the returning light. The microscopic structures of living tissue may be acquired based on a combination of the principles of white light interferometry and confocal microscopy.

Whereas the imaging for intravascular optical coherence tomography in its early stages was not as fast as for intravascular ultrasound techniques and thus was not widely utilized, the recently developed second-generation intravascular optical coherence tomography technology has improved speed by tenfold and more, enabling the imaging of a blood vessel within several seconds. Since light is used, images are obtained while flushing the blood with a mixture of a saline solution and a contrast agent in order to minimize the effect of the blood. Since the resolution is improved by about 10 times (~10 µm) compared to intravascular ultrasound techniques, it is possible to observe minute changes in the blood vessel. Recently, multifunctional imaging techniques that incorporate fluorescence imaging technology have been implemented at the laboratory level.

In order to transmit the light to the catheter or to transmit the light that has been inputted to the catheter, a collimator for forming collimated beams may be employed, where the collimator may be used in the form of light-transmitting optical fibers joined together. Prior art documents related to this include Korean Patent Publication No. 2001-0108141.

A collimator is mainly used in conjunction with a single-mode fiber or a double-clad fiber, and the refractive index profiles for the core, cladding, and coating layers, which make up the single-mode fiber and double-clad fiber, are as shown in FIG. 1. In the case of a single-mode fiber (FIG. 1(a)), the light is guided only through the core, and therefore in order to enable total internal reflection in interface between the core and cladding only, the order of the refractive indexes is the core, coating layer, and cladding from highest to lowest. In contrast, in the case of a double-clad fiber (FIG. 1(b)), the light is guided not only through the core but also through the cladding, so that the order of the refractive indexes is the core, cladding, and coating layer from highest to lowest. In The light guided through the cladding of a double-clad fiber that is joined to a collimator can be coupled to the core of a single-mode fiber or double-clad fiber that is connected to another collimator, but the coupling between the core and the cladding can incur noise in the scanned images of a sample.

SUMMARY OF THE INVENTION

The present invention is to provide a collimator and an imaging catheter system including the collimator that are capable of reducing noise in the scanned images of a catheter device.

To achieve the objective above, an embodiment of the present invention provides a noise-attenuating collimator using a double-clad fiber, where the noise-attenuating collimator includes: a transparent tube, into which the coating-less region of the double-clad fiber is inserted, and of which the diameter is larger than the diameter of the cladding of the double-clad fiber; and a first resin layer, which is coated on the exterior of the transparent tube, and of which the refractive index is lower than the refractive index of the transparent tube.

Also, to achieve the objective above, another embodiment of the present invention provides a noise-attenuating collimator using a double-clad fiber, where the noise-attenuating collimator includes: a housing, which connects with a first double-clad fiber, and into which a second double-clad fiber is inserted therein, with the second double-clad fiber including a cladding that has a diameter larger than the diameter of a cladding of the first double-clad fiber; and a lens.

Also, to achieve the objective above, still another embodiment of the present invention provides an imaging catheter system that includes: at least one or more light source; a noise-attenuating collimator configured to transmit light from the light source by using a first double-clad fiber; and a catheter device configured to receive the light as input from the noise-attenuating collimator to scan a sample, where the noise-attenuating collimator reduces noise in a scanned image by decreasing the density of light guided through the cladding of the first double-clad fiber.

Embodiments of the present invention can reduce noise in the scanned images by causing the light guided in the cladding of a double-clad fiber to be guided in a cladding of a larger diameter to thereby lower the density of the light guided in the cladding.

BRIEF DESCRIPTION OF THE DRAWINGS

FIG. 2 is a diagram illustrating an imaging catheter system.

FIG. 3 is a diagram illustrating a collimator.

FIG. 4 is a diagram illustrates noise that can occur in an imaging catheter system.

FIG. 5 is a diagram illustrating a noise-attenuating collimator using a double-clad fiber according to an embodiment of the present invention.

FIG. 6 is a diagram illustrating a noise-attenuating collimator using a double-clad fiber according to another embodiment of the present invention.

FIG. 7 is a diagram illustrating an imaging catheter system according to another embodiment of the present invention.

FIG. 8 is a diagram illustrating the noise attenuation effect of an imaging catheter system according to another embodiment of the present invention.

DETAILED DESCRIPTION OF THE INVENTION

Figure 1:
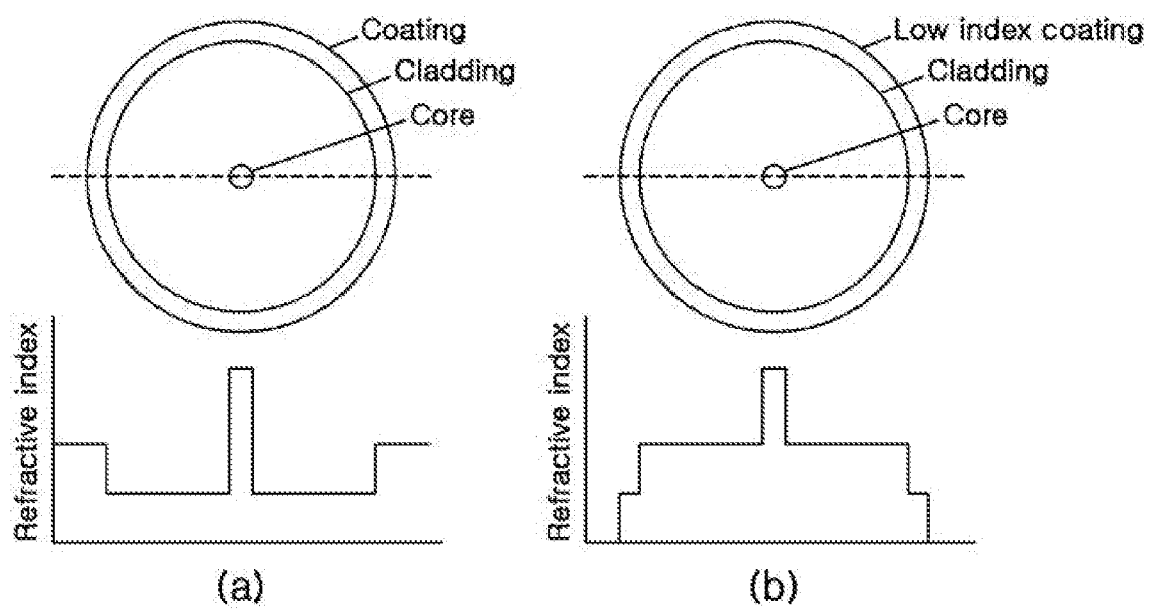
FIG. 1 illustrates diagrams of refractive index profiles for a single-mode fiber and a double-clad fiber.

As the invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In describing the drawings, similar reference numerals are used for similar elements.

Certain embodiments of the present invention are described below in more detail with reference to the accompanying drawings.

FIG. 2 is a diagram illustrating an imaging catheter system and illustrates an imaging catheter system based on optical coherence tomography (OCT) and near-infrared fluorescence (NIRF) imaging. FIG. 3 is a diagram illustrating a collimator, and FIG. 4 is a diagram illustrates noise that can occur in an imaging catheter system.

Referring to FIG. 2, the imaging catheter system may include an OCT (optical coherence tomography) light source 210, a near-infrared fluorescence light source 220, a stationary part 230, and a rotating part 250.

The stationary part 230 may be the part that is stationary even when the catheter 255 is rotated and may include a first and a second collimator 231, 232 that transmit light from the near-infrared fluorescence light source 220 and the OCT light source 210, optics for transmitting the light outputted from the first and second collimator 231, 232 to the rotating part 250 and transmitting the light transmitted from the rotating part 250 to the PMT 241, and a PMT (photomultiplier tube) detector 241 for detecting beams with very high sensitivity in the ultraviolet, visible ray, and near-infrared regions of an electromagnetic field. The optics may include dichroic mirrors 235, 236, a reflective mirror 237, a lens 238, optical filters 239, 240, etc.

The rotating part 250 may be the part that rotates together with the catheter and may include a third collimator 251 for transmitting light inputted from the stationary part 230 to the catheter 255 and outputting the light inputted to the catheter 255 back to the stationary part 230, a catheter 255 that is inserted into a sample 257 to scan the sample, and an optical connector 253 that connects the third collimator 251 and the catheter 255. The catheter may be an expendable device and can be readily fastened and separated by way of the optical connector.

To be more specific, a laser outputted from the OCT light source 210 may be inputted through a single-mode fiber 233 to the first collimator 231. A laser outputted from the near-infrared fluorescence imaging light source 220 may be inputted through a single-mode or a multi-mode fiber 234 to the second collimator 232. The laser of the OCT light source 210 can have a central wavelength of 1290 nm, and the laser of the near-infrared fluorescence imaging light source 220 can have a central wavelength of 780 nm. The light outputted from the first and second collimator 231, 232 can be inputted to the third collimator 251 of the rotating part 250 via dichroic mirrors 235, 236, which reflect or pass light according to wavelength.

The light inputted to the third collimator 251 may be inputted to the optical connector 253 via a double-clad fiber 252 and transmitted to the catheter 255. The catheter 255 may output light towards a sample 257, such as a blood vessel for example, to scan the sample 257, and the light returning from the sample 257 may be inputted again via the optical connector 253 to the third collimator 251. From among the light outputted from the third collimator 251, light of the OCT wavelength may return via the same path to the first collimator 231, and light of the near-infrared fluorescence wavelength may be transmitted by the dichroic mirrors 235, 236 and the reflective mirror 237 to the photomultiplier tube detector 241. Here, optical filters 239, 240 can be used on the path of the near-infrared fluorescence imaging laser to increase the signal-to-noise ratio of the near-infrared fluorescence image signals.

That is, the lasers outputted from the near-infrared fluorescence imaging light source 220 and the OCT light source 210 may be transmitted past the stationary part 230 and rotating part 250 to the sample 257, and from among the light returning from the sample 257, the light of the OCT wavelength may return to the first collimator 231 via the same path, and the light of the near-infrared fluorescence wavelength may be inputted to the photomultiplier tube detector 241.

Referring to FIG. 3, the collimator may include a housing 310, a first glass tube 330 in which an optical fiber 320 is inserted, and a second glass tube 340 that includes a lens. An air gap or a resin layer, etc., can be present between the first glass tube 330 and the second glass tube 340, and a GRIN lens can be used for the lens. Light transmitted through the optical fiber 320 may be outputted via the lens, and light inputted to the lens may be condensed by the lens and transmitted to the optical fiber 320. The first and second collimators 231, 232 may have single-mode fibers 233, 234 joined with first glass tubes 330, and the third collimator 251 may have a double-clad fiber 252 joined with a first glass tube 330.

Since it is impossible to perfectly align the first and second collimators 231, 232 with the third collimator 251 to an ideal alignment, the light outputted from the first and second collimators 231, 232 may be coupled not only with the core of the double-clad fiber 252 inserted in the third collimator 251 but also partially with the cladding. Such occurrence of the light guided through the core of the optical fiber being coupled to the cladding (core-cladding coupling) can also appear between the third collimator 251 and the optical connector 253. Conversely, there can also occur a type of coupling in which the light being guided through the cladding is guided to the core.

When the light that was coupled to the cladding at a point of core-cladding coupling is coupled again and guided to the core at a point of core-cladding coupling, this can incur noise 410 such as that shown in FIG. 4 (noise caused by a double clad fiber) in the optical coherence tomography images due to differences in optical distances of the light guided in the core and the cladding.

For removing or reducing such noise, methods of adjusting the contrast of the scanned images (optical coherence tomographic images) or adjusting the length of the double-clad fiber can be considered.

However, if the contrast is adjusted, there is a risk that not only noise but also information that does not include noise may be lost as well.

Also, since the optical distance of the light guided through the cladding is larger than the optical distance of the light guided through the core, increasing the length of the double-clad fiber to several meters can remove the noise component in the optical coherence tomographic images, because the light guided through the cladding is excluded in the optical coherence tomographic images, but in order to manufacture a rotating part that is capable of high speed rotations for clinical use, the length of the double-clad fiber between the collimator and the optical connector generally has to be within several hundred millimeters. Also, since the double-clad fiber used in a catheter also has to be manufactured to be within 2 m for stable rotation, there is difficulty in actually increasing the length of the double-clad fiber.

Thus, the present invention proposes a collimator that can remove noise in the optical coherence tomographic images by lowering the density of light guided through the cladding, i.e. reducing the cause of the noise. The present invention can lower the density of light guided through the cladding and thus remove noise by allowing the light guided through the cladding of a double-clad fiber to be guided in a cladding having a larger diameter. When light being guided in a first cladding due to the numerical aperture limit of the optical fiber core is made to be guided in a second cladding that has a larger diameter than the diameter of the first cladding, the light guided in the second cladding cannot easily be coupled again to the core, and therefore noise caused by the coupling between the core and the cladding can be removed or attenuated.

FIG. 5 is a diagram illustrating a noise-attenuating collimator using a double-clad fiber according to an embodiment of the present invention, where the collimator can be adopted as the third collimator described above.

Referring to FIG. 5, a noise-attenuating collimator based on the present invention may include a transparent tube 510 and a first resin layer 520. In certain embodiments, a second resin layer 530 and a housing 540 can additionally be included.

Into the transparent tube 510, a coatingless region 574 of a double-clad fiber 570 may be inserted, the transparent tube 510 being a tube having a larger diameter than the diameter of the cladding 572 of the double-clad fiber 570. The coating layer 571 of the double-clad fiber 570 can be removed by a mechanical or a chemical method, etc., and the coatingless region 574 consisting of the cladding 572 and the core 573 may be inserted into the transparent tube 510.

The light guided in the cladding 572 can be guided into the transparent tube 510, and since the diameter of the transparent tube 510 is larger than the diameter of the cladding 572, the density of the light guided in the transparent tube 510 can be lowered compared to the cladding 572, resulting in reduced noise in the scanned images. In an embodiment of the invention, the diameter of the cladding 572 can be 0.125 nm, and the diameter of the transparent tube 510 can be 0.4 nm.

In order that the light guided in the cladding 572 of the double-clad fiber 570 may be guided into the transparent tube 510, it may be preferable to have the refractive index of the transparent tube 510 be the same as the refractive index of the cladding 572 of the double-clad fiber 570, but as long as the refractive indexes enable the light guided in the cladding 572 of the double-clad fiber 570 to be guided into the transparent tube 510, it may be permissible to have the refractive index of the transparent tube 510 be greater than the refractive index of the cladding 572. That is, the refractive index of the transparent tube 510 can be greater than or equal to the refractive index of the cladding 572, and in an embodiment of the invention, the transparent tube 510 can be a borosilicate tube.

The first resin layer 520 may be coated on the exterior of the transparent tube 510 and may be a resin layer having a refractive index smaller than that of the transparent tube 510. That is, the first resin layer 520 may enable total internal reflection of the light guided in the transparent tube 510, to prevent the light guided in the transparent tube 510 from leaking out of the transparent tube 510.

Since the double-clad fiber 570 may not be able to function normally when the coating layer 571 of the double-clad fiber 570 is removed and the cladding 572 is exposed to the exterior, it may be preferable that the length of the transparent tube 510 be longer than the length of the coatingless region 574 to allow a portion of the coating layer 571 to be inserted into the transparent tube 510 such that the cladding 572 is not exposed. In this case, the cladding 572 part that has a relatively lower strength can be completely inserted inside the transparent tube 510, and the double-clad fiber 570 can be protected from damage.

Also, in certain embodiments, a second resin layer 530 can be included between the coatingless region 574 and the transparent tube 510, where the second resin layer 530 may attach the coatingless region 574 with the transparent tube 510. Here, in order that the light being guided in the cladding 572 may be guided to the transparent tube 510, it may be preferable that the refractive index of the second resin layer 530 also be the same as the refractive index of the cladding 572 or greater than the refractive index of the cladding 572. In an embodiment of the invention, the refractive index of the cladding 572 can be 1.46, the refractive index of the transparent tube 510 and the second resin layer 530 can be 1.48, and the refractive index of the first resin layer 520 can be the refractive index of the coating layer 571.

The transparent tube 510 can be inserted in and secured to the housing 540, where the housing 540 can be, for example, a glass tube or a ceramic ferrule. A glass tube 550 that includes the housing 540 and a lens can be inserted into another housing 560 to become a collimator of the form described with reference to FIG. 3.

The resin layers described above can be of an epoxy resin, where UV epoxy can be used for convenient manufacture.

FIG. 6 is a diagram illustrating a noise-attenuating collimator using a double-clad fiber according to another embodiment of the present invention, where the collimator can be adopted as the third collimator described above.

Referring to FIG. 6, a noise-attenuating collimator based on the present invention may include a housing 650 and a lens.

A second double-clad fiber 610 may be inserted in the housing 650, where the second double-clad fiber 610 may be connected with a first double-clad fiber 640, and the diameter of the second cladding 620 of the second double-clad fiber 610 may be larger than the diameter of the first cladding 642 of the first double-clad fiber 640.

The light guided in the first cladding 642 can be guided to the second cladding 630, and since the diameter of the second cladding 630 is larger than the diameter of the first cladding 642, the density of the light guided in the second cladding 630 can be lowered compared to the first cladding 642, whereby noise can be reduced in the scanned images. In an embodiment of the invention, the diameter of the first cladding 642 can be 0.125 nm, and the diameter of the second cladding 630 can be 0.4 nm.

In order that the light guided in the first cladding 642 may be guided to the second cladding 630, it may be preferable to have the refractive index of the second cladding 630 be the same as the refractive index of the first cladding 642. Compared with the embodiment of FIG. 5, the embodiment of FIG. 6 is of a form analogous to two double-clad fibers joined together, and as such, can be implemented by using a double-clad fiber that includes a cladding having the same refractive index but different diameters.

For easier manufacture, the second double-clad fiber 610 can be inserted into the housing 650 with the coating layer removed, in which case the housing 650 and the second double-clad fiber 610 can be attached together with a resin. That is, the coating layer of the second double-clad fiber 610 can be a resin layer 620 that attaches the housing 650 with the second double-clad fiber 610. The resin layer 620 can be of an epoxy resin, where UV epoxy can be used for convenient manufacture.

The housing 650 can be, for example, a glass tube or a ceramic ferrule. A glass tube 660 that includes the housing 650 and a lens can be inserted into another housing 670 to become a collimator of the form described with reference to FIG. 3.

FIG. 7 is a diagram illustrating an imaging catheter system according to another embodiment of the present invention, and FIG. 8 is a diagram illustrating the noise attenuation effect of an imaging catheter system according to another embodiment of the present invention.

Referring to FIG. 7, an imaging catheter system based on the present invention may include at least one or more light source 710, a stationary part 720, and a rotating part 730. An imaging catheter system based on the present invention can be of a form that includes a collimator described with reference to FIGS. 5 and 6 joined to the imaging catheter system described with reference to FIG. 2.

The light source can differ according to the technology applied to the imaging catheter system. In the case of an imaging catheter system based on optical coherence tomography and near-infrared fluorescence imaging technology as described above for FIG. 2, a near-infrared fluorescence imaging light source and an OCT light source can be used as the light sources. In different embodiments, an imaging catheter system according to the present invention can be based on optical coherence tomography-fluorescence imaging technology, optical coherence tomography-spectroscopy, optical coherence tomography-autofluorescence imaging, optical coherence tomography-fluorescence lifetime imaging. Alternatively, the imaging catheter system can use just the OCT light source.

The light outputted from the light source 710 may be transmitted via the stationary part 720 to the rotating part 730. Conversely, the light inputted from the sample may be transmitted via the rotating part 730 to the stationary part 720.

The noise-attenuating collimator 731 of the rotating part 730 may transmit the light of the light source to the catheter device 733 by using a double-clad fiber, and the catheter device 733 may receive the light from the noise-attenuating collimator 731 as input to scan the sample. The noise-attenuating collimator 731 can reduce noise in the scanned image by reducing the density of the light guided through the cladding of the double-clad fiber.

While FIG. 7 is described using an imaging catheter system as an example, a noise-attenuating collimator based on the present invention can be applied not only to an imaging catheter system but also to any of a variety of imaging systems that transmits light with an optical fiber to generate a scanned image of a sample. Here, the catheter device 733 of FIG. 7 can be substituted by any one of various types of scanning devices that scans the inside or outside of a sample.

FIG. 8(a) shows an optical coherence tomographic image from an imaging catheter system using the third collimator with a single-mode fiber joined, FIG. 8(b) shows an optical coherence tomographic image from an imaging catheter system using the third collimator with a double-clad fiber joined, and FIG. 8(c) shows an optical coherence tomographic image from an imaging catheter system using a collimator based on the present invention.

Referring to FIG. 8, it can be seen that noise occurs in the optical coherence tomographic images when double-clad fibers are used, and it can be plainly seen that there is less noise in the image of FIG. 8(c) compared to FIG. 8(b). The case shown in FIG. 8(b) has noise of about 30 dB, whereas the case shown in FIG. 8(c) has noise of about 13 dB.

While the present invention is described above by way of limited embodiments and drawings that refer to particular details such as specific elements, etc., these are provided only to aid the general understanding of the present invention. The present invention is not to be limited by the embodiments above, and the person having ordinary skill in the field of art to which the present invention pertains would be able to derive numerous modifications and variations from the descriptions and drawings above. Therefore, it should be appreciated that the spirit of the present invention is not limited to the embodiments described above. Rather, the concepts set forth in the appended scope of claims as well as their equivalents and variations are encompassed within the spirit of the present invention.

What is claimed is:

1. A noise-attenuating collimator using a double-clad fiber, the noise-attenuating collimator comprising:
   a transparent tube configured to receive a coatingless region of the double-clad fiber inserted therein, the transparent tube having a diameter larger than a diameter of a cladding of the double-clad fiber;
   a first resin layer coated on an exterior of the transparent tube, the first resin layer having a refractive index lower than a refractive index of the transparent tube;
   a second resin layer disposed between the coatingless region and the transparent tube; and
   a housing configured to receive the transparent tube inserted therein,
   wherein refractive indexes of the transparent tube and the second resin layer are higher than or equal to a refractive index of the cladding so that light guided through the cladding can be guided to the transparent tube.

2. The noise-attenuating collimator of claim 1, wherein a length of the transparent tube is longer than a length of the coatingless region, and
   a portion of a coating layer of the double-clad fiber is inserted into the transparent tube.

3. An imaging catheter system comprising:
   at least one or more light source;
   a noise-attenuating collimator configured to transmit light from the light source by using a double-clad fiber; and
   a catheter device configured to receive the light as input from the noise-attenuating collimator to scan a sample,
   wherein the noise-attenuating collimator comprises:

a transparent tube configured to receive a coatingless region of the double-clad fiber inserted therein, the transparent tube having a diameter larger than a diameter of a cladding of the double-clad fiber;

a first resin layer coated on an exterior of the transparent tube, the first resin layer having a refractive index lower than a refractive index of the transparent tube;

a second resin layer disposed between the coatingless region and the transparent tube; and a housing configured to receive the transparent tube inserted therein, wherein refractive indexes of the transparent tube and the second resin layer are higher than or equal to a refractive index of the cladding so that light guided through the cladding can be guided to the transparent tube.

4. The imaging catheter system of claim 3, wherein a length of the transparent tube is longer than a length of the coatingless region, and a portion of a coating layer of the double-clad fiber is inserted into the transparent tube.

\* \* \* \* \*